United States Patent [19]

Wong

[11] Patent Number: 4,526,578

[45] Date of Patent: Jul. 2, 1985

[54] VAGINAL DIAPHRAGM

[75] Inventor: Patrick S. L. Wong, Hayward, Calif.

[73] Assignee: ALZA Corporation, Palo Alto, Calif.

[21] Appl. No.: 494,700

[22] Filed: May 16, 1983

[51] Int. Cl.³ ............................................. A61F 5/46
[52] U.S. Cl. .................................. 604/892; 128/127; 128/130; 128/132 R
[58] Field of Search ............... 604/892; 128/127, 130, 128/131, 132

[56] References Cited

U.S. PATENT DOCUMENTS 3,036,570  5/1962  Milgrom et al. .................. 128/127
4,261,352  4/1981  Sedlacek ........................... 128/127
4,286,587  9/1981  Wong ................................. 128/127
4,286,593  9/1981  Place et al. ........................ 604/93
4,292,965  10/1981 Nash et al. ..................... 128/127 X Primary Examiner—John D. Yasko
Assistant Examiner—Christa K. Scott
Attorney, Agent, or Firm—Paul L. Sabatine; Edward L. Mandell; Steven F. Stone

[57] ABSTRACT

A vaginal diaphragm is disclosed comprising an annular reservoir housing a beneficial agent, and in a preferred embodiment the diaphragm film embraces a means for containing and releasing a beneficial agent.

25 Claims, 8 Drawing Figures

VAGINAL DIAPHRAGM

FIELD OF THE INVENTION

This invention relates to a vaginal diaphragm. More particularly, this invention pertains to a vaginal diaphragm that delivers a vaginally acceptable useful agent at a controlled rate to a vagina for the prevention of fertilization, and/or for the prevention of acquiring a social disease.

BACKGROUND OF THE INVENTION

The vaginal diaphragm, as currently designed, has been used since the beginning of the 19th century for the prevention of fertilization. The vaginal diaphragm was invented, following the invention of the vulcanization of rubber, by Freidrick Wilde in 1832. However, credit for its invention is usually and erroneously given to C. Hasse. In 1882, Hasse, fearful that his professional and academic reputation would be jeopardized by his publishing an article pertaining to the vaginal diaphragm, titled "Ueber Faculative Sterililat", published the article under the pseudonym, Wilhelm P. J. Mensinga. This paper on "facultative sterility", FS, was a treatise in support of controlling fertility and it listed three inidcations for using "facultative sterility". The indications were (1) permanently in the case of incapacity to bear children, (2) for a longer undetermined period of time in case of syphilis and other constitutional diseases, and (3) for a definite period of time as in cases concerning a failure of lactation. Shortly after the work of Hasse became known, the vaginal diaphragm became popular in both Europe and in the United States, and to this day Wihlem Mensinga is credited with inventing the vaginal diaphragm in 1882.

Many attempts have been made by the prior art to increase the effectiveness of the vaginal diaphragm. For example, in U.S. Pat. No. 2,551,618 the patentee Mayer discloses a pessary of the vaginal diaphragm type consisting of a cup-shaped body having an annular wall with the improvement consisting of a solid, substantially conical stud for insertion into the cervical orifice. The stud is used in an orifice-closing relation with the uterus for sanitary and hygienic purposes. U.S. Pat. No. 2,580,133 issued to Sheen discloses a pessary-diaphragm that is useful for treating infections at the orifice of the uterus. The treatment consists in placing a medicament in the cavity area of the pessary-diaphragm, which cavity is positioned over the cervical orifice to achieve the intended result. U.S. Pat. Nos. 4,198,976; 4,200,090; and 4,219,016 issued to Dorbish et al disclose a vaginal contraceptive device consisting of a dish-shaped reservoir containing a spermicide for releasing into a vagina for achieving contraception. U.S. Pat. No. 4,286,593 issued to Place et al discloses a vaginal contraceptive shield comprising a rod-like support containing a spermicide for releasing in a vagina. U.S. Pat. No. 4,326,510 issued to Buckles discloses a vaginal barrier contraceptive torus consisting of a pair of overlapping, unsealed flaps for letting fluid drain from the cervix and for releasing a spermicide for its known effects. U.S. Pat. No. 4,332,243 issued to Gutnick discloses a contraceptive diaphragm consisting of a pouch or sac, and individual, refillable chambers inside a rim, which release an active agent from the chambers and then through the rim for preventing disease and for preventing conception.

While the above vaginal, physical contraceptives seemingly represent advancements in the vaginal contraceptive art, there are serious disadvantages associated with both their design and their use. For example, the vaginal diaphragms disclosed in the above identified U.S. Pat. Nos. 2,551,618; 2,580,133; 4,198,976; 4,200,090; and 4,219,016 are not a reliable method of birth control in view of the scientific evaluation presented in an article titled, "Why The Diaphragm Doesn't Work", as published by Berkowitz in *San Francisco*, Vol. 23, No. 12, pages 72, 74 and 75, 1981. In view of the article, these diaphrams are not reliable because for a diaphragm to block the passage of sperm, the diaphragm must be fitted approximately to the diameter of the vagina near the opening of the cervix. Thus, since only a minute amount of ejaculate is needed for fertilization, and since the shape of the vagina varies during intercourse and orgasm, it is easy for a sperm to swim around the diaphragm and gain access to the opening of the cervix. This can lead to an unwanted fertilization, as there is a margin of error built into the concept of the diaphragm. The contraceptive shields as disclosed in U.S. Pat. Nos. 4,286,593 and 4,326,510 possess the structural disadvantage that they may lose contact with the walls of the vagina, as the vagina expands during sexual excitement, and the shield may be displaced concomitantly. These in vivo activities make it possible for a sperm to travel around the shield and gain entrance into the uterus. The vaginal diaphragm disclosed in U.S. Pat. No. 4,332,243 consisting of a sac or chambers that release into a rim are cumbersome to manufacture, it is difficult to refill the chambers, and the presence of the chambers precludes the diaphragm from being made with a tension member that is needed in many instances for manufacturing the diaphragm in proper position in the the vagina.

It will be appreciated by those skilled in the art, that if a vaginal diaphragm is provided that can cover the cervix and concomitantly deliver a vaginally acceptable useful agent around the entrance of the cervix, such a diaphragm would have a positive value and satisfy a long-felt need. Likewise, it will be further appreciated that if a method is provided that uses an occlusive diaphragm that delivers a useful agent for preventing fertilization, and/or lessening the possibility of acquiring a social disease, such a method would represent a substantial contribution and advancement in the practicing art.

OBJECTS OF THE INVENTION

It is an object of this invention to provide a vaginal diaphragm which obviates the above mentioned disadvantages and difficulties associated with prior art.

Another object of the invention is to provide an improved vaginal diaphragm that is easily insertable as an occlusive diaphragm and additionally delivers a useful agent in the vagina for preventing conception and/or for preventing acquiring a social disease.

Yet another object of the invention is to provide a novel and useful vaginal diaphragm which is simple in construction, economically manufactured, convenient to use, is reusable, or optionally disposable.

Yet still another object of the invention is to provide a vaginal diaphragm that on positioning in the vagina closes the opening of the cervix, and when in position delivers a useful agent around the opening of the cervix.

It is a further object of this invention to provide a novel vaginal diaphragm that comprises a film member for closing the entrance of the cervix, and a peripheral film member, which reservoir member houses an active agent and delivers the agent around the entrance of the cervix.

It is a further object of this invention to provide a novel and useful diaphragm that comprises a film member for closing the entrance of the cervix, which film member contains an active agent and a peripheral reservoir member associated with the film member, which film member contains an active agent, with the diaphragm film member releasing agent into the vagina, and the peripheral member concurrently releasing agent around the entrance of the cervix, when the diaphragm is in a vagina.

Yet another object of the invention is to provide a vaginal diaphragm comprising a peripheral reservoir comprising an active agent formulation and a tension member for producing a spring-tension effect for holding the diaphragm within the vagina.

Other objects, features, and advantages of the invention will be more apparent to those skilled in the art from the following detailed specification taken in conjunction with the drawing figures and the accompanying claims.

BRIEF DESCRIPTION OF THE DRAWINGS

In the drawing figures which are not drawn to scale, but are set forth to illustrate various embodiments of the invention, the drawing figures are as follows.

In the drawing figures, and in the specification, like parts in related figures are identified by like parts. The terms appearing earlier in the specification and in the description of the drawing figures, as well as embodiments thereof, are further detailed elsewhere in the disclosure.

DETAILED DESCRIPTION OF THE INVENTION

Figure 1:
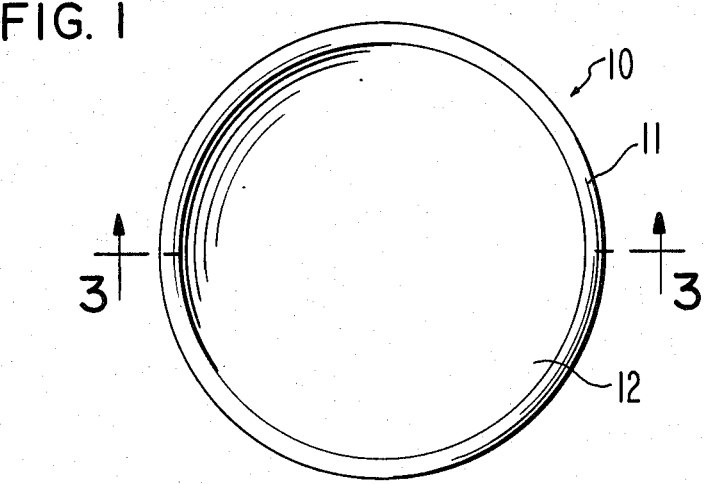
FIG. 1 is a top view of a vaginal diaphragm provided by the invention.

Turning now to the drawing figures in detail that are an example of the vaginal diaphragm provided by the invention, and which example is not to be construed as limiting, the presently preferred vaginal diaphragm is seen in FIG. 1, as indicated by the numeral 10. In FIG. 1, vaginal diaphragm 10 comprises an outer peripheral, annular reservoir 11, and a thin film 12. Film 12 extends across the space internally bounded by the inner periphery of reservoir 11. Film 12 is seen as integrally formed with annular reservoir 1. Film 12 generally is cup-shaped or dome-shaped, and preferably made from a flexible, non-toxic, vaginally acceptable material. Vaginal diaphragm 10 is shaped and adapted to fit snugly in the vaginal space between the posterior aspect of the pubis and the cul-de-sac in such a way that cup-shaped or dome-shaped film 12 covers the cervix and the better part of the anterior vaginal wall. Annular reservoir comprises in general circular, oval, discoid or peripheral ring shapes suitably shaped and adapted for placement in the vaginal cul-de-sac, posterior and inferior to the cervix.

Figure 2:
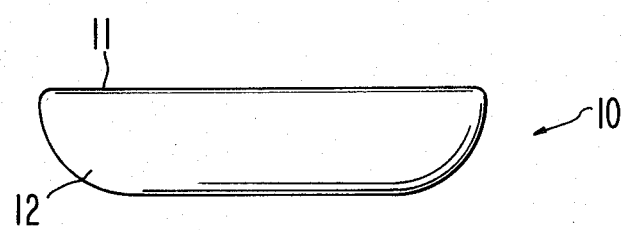
FIG. 2 is a side view of the vaginal diaphragm of FIG. 1.
Figure 3:
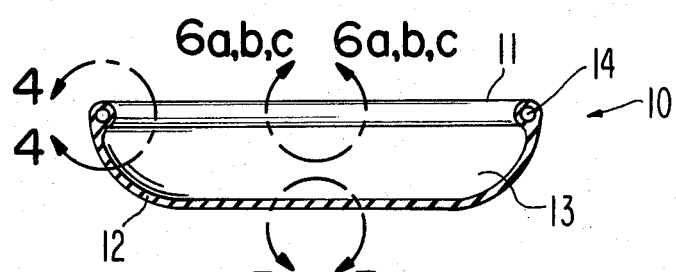
FIG. 3 is a cross-sectional view of the vaginal diaphragm of FIG. 1, taken through 3—3 of FIG. 1 for depicting the structure of the vaginal diaphragm.

FIG. 2 and 3 are an elevational view of vaginal diaphragm 10 of FIG. 1. In FIG. 2, a side view, diaphragm 10 comprises annular reservoir 11 and flexible film 12. In FIG. 3, diaphragm 10 is seen in cross-section comprising annular reservoir 11, and film 12 that forms and defines cup-shaped or dome-shaped cervical receiving area 13. Annular reservoir 11 comprises an internal lumen 14 for containing an active agent formulation as seen in FIG. 4.

Figure 4:
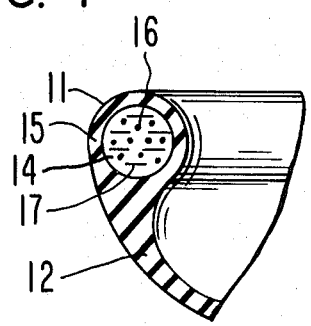
FIG. 4 is an enlarged sectional view of the vaginal diaphragm through 4—4 of FIG. 3 for illustrating the reservoir of the diaphragm for containing an active agent.

FIG. 4 is a sectional view of diaphragm 10 through 4—4 of FIG. 3. FIG. 4 is a cross-section through annular reservoir 11, associated with a cross-section of film 12 secured to annular reservoir 11. Annular reservoir 11 comprises a wall 15 surrounding internal lumen 14 containing active agent formulation 16, identified by dots. Wall 15 is a rate controller formed of a thermoplastic polymer, or a thermoset polymer, of the diffusional or microporous type. Rate controller wall 15 maintains the prescribed rate of agent formulation 16 released from diaphragm 10. Agent formulation 16 can be in lumen 14 alone or with an inner mass transfer conductor 17, identified by dashes, that aids in releasing an active agent from diaphragm 10. A description of active agents and mass transfer conductors appears later in the specification.

Figure 5:
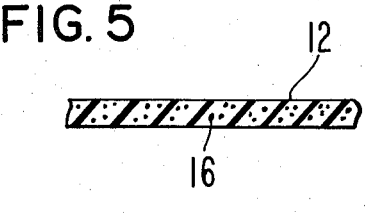
FIG. 5 is an enlarged sectional view of the vaginal diaphragm through 5—5 of FIG. 3 for illustrating the film member of the diaphragm containing an active agent; and, FIG. 6a, b, and c are enlarged sectional views of the vaginal diaphragm through 6a, b and c for depicting structural embodiments of the diaphragm comprising means for forming the reservoir, and tension means for aiding in maintaining the diaphragm in a vagina.

FIG. 5 is a cross-section of film 12 through section 5—5 of FIG. 3. Film 12 is formed of a polymeric material that is flexible, impervious to the passage of sperm, and in a preferred embodiment it contains an active agent formulation 16. Active agent formulation 16 is released from diaphragm 10 when diaphragm 10 is in the biological environment of use. Active agent formulation 16 in film 12 can be the same as active agent formulation 12 in annular reservoir 11, or active agent formulation 16 in film 12 can be different than active agent formulation 16 in annular reservoir 11.

Figure 6A:
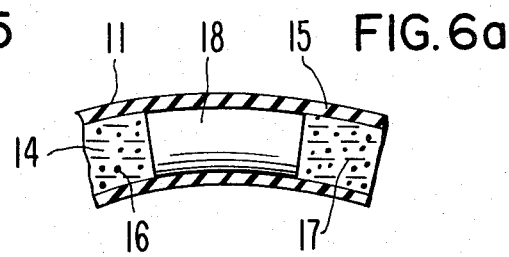
Figure 6B:
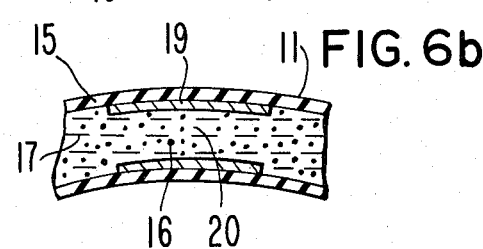

FIGS. 6a and 6b are cross-section views through 6a,b—6a,b of FIG. 3. FIGS. 6a and 6b illustrate a coupling member used for forming annular reservoir 11, when annular reservoir 11 is made from a tubular member having a pair of ends joined to define a closed internal lumen. In FIG. 6a, annular reservoir 11 comprises wall 15 that surrounds and forms internal lumen 14. Internal lumen 14 or internal space 14 contains agent formulation 16 and mass transfer conductor 17. Annular reservoir 11 comprises a coupling member 18 made for uniting annular reservoir 11 into a single annular shaped system. In FIG. 6a, coupling member 18 is formed of a solid material placed inside annular reservoir 11 to form an end-to-end, fluid-tight connection, for successful use of diaphragm 10 during release of agent formulation 16.

FIG. 6b is similar to 6a, with all the numbers as described in FIG. 6a, except for the numbers discussed described in FIG. 6a, except for the numbers discussed immediately below. In FIG. 6b, number 19 is a coupling member used as an internal connector for joining the ends of a tube member into an end-to-end essentially fluid leak-proof joint. Coupline 19, in the embodiment illustrated, has a passageway 20 therethrough that permits the passage of a liquid mass transfer conductor 17 containing active agent 16 to flow in annular reservoir 11. Coupling member 19 is in mated relation with the inside of reservoir 11 to form an essentially liquid-tight-union.

Figure 6C:
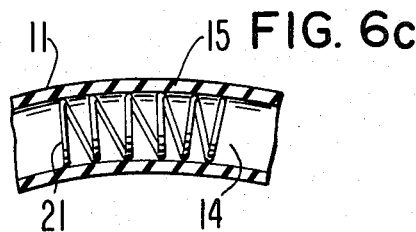

FIG. 6c is a cross-section through 6c—6c of FIG. 3. FIG. 6c illustrates a spring 21 in the internal lumen 14 of annular reservoir 11. The spring is used for aiding in positioning the diaphragm in the vagina, and as a tension member. for keeping the diaphragm in the vagina and for providing tension against the vaginal wall. The spring can be a flat compressible watchspring, a coil spring possessing a wire spiral configuration, an arcing spring and the like. The use of a flat spring makes it possible to fold the diaphragm for easy insertion past the cervix into the posterior fornix; the wire spiral spring is flexible in all planes. This feature increases the insertability of the diaphragm, and the arcing spring operates in a like manner.

The vaginal diaphragm of the invention can be provided in various sizes. The size of the diaphragm is given by the diameter of the annular reservoir, expressed in millimeters, mm. The vaginal diaphragm is provided in sizes of from 40 mm to 110 mm in variations of 5 mm. The most common size is between 70 mm and 80 mm.

DETAILED DESCRIPTION FOR PROVIDING THE INVENTION

In accordance with the practice of the invention, it has now been found vaginally acceptable polymerice materials of the diffusional or the microporous types can be used for manufacturing the vaginal diaphragm. The polymeric materials used are substantially free of any adverse affects on the vagina. The vagina is lined with extremely delicate tissues, and it is essential therefore, that materials forming diaphragm 10 do not adversely affect the vagina. The diffusional materials and the microporous used for the purpose of this invention are the vaginally compatible materials set forth below. By compatible is meant the materials are pharmaceutically acceptable within the environment of the vagina and generically to the host. That is, these materials do not break down in the vagina, there is no absorption of the materials, there is no deleterious actions on the sensitive tissues in the area of placement and retention of the diaphragm over a prolonged period of time, and the materials do not harm the active agent and inner mass transfer conductor in the diaphragm.

The diffusional polymers suitable for the purpose of this invention include polymers, copolymers, terpolymers and the like, that are capable of being softened by heat, and hardened by cooling through a temperature range characteristic of the polymer, its crystalline melting or glass transition polymer, its crystalline melting or glass transition temperature. In the softened state they can be shaped by flow into annular reservoirs and films by vacuum forming, molding, extrusion and like techniques. The changes for these materials upon heating is substantially physical. One example of a polymer that can be used for the present purpose is styrene-butadiene block copolymer. The styrene-butadiene block copolymer useful for manufacturing the annular reservoir and the film include those generally formed by initiation at a chain end of an already formed polymeric chain. The block copolymers are thermoplastic elastomers because of their ability to become fluid and moldable at elevated temperatures. These properties lend themselves to manufacture of diaphragm 10. Generally, the styrene of the block copolymer will have a molecular weight in the range of 10,000 to 20,000, and the butadiene will have a molecular weight in the range of 40,000 to 100,000. The styrene-butadiene block copolymers suitable for the present purpose are permeable to active agent, including spermicide, germicide, viuride, and the like.

Additional presently preferred polymers that can be used for manufacturing diaphragm 10 include poly(methylacrylate), poly(butylmethacrylate), plasticized poly(vinylchloride), plasticized nylon, plasticized soft nylon, plasticized poly(ethyleneterephthalate), poly(ethylene), poly(acrylonitrile), poly(trifluorochloroethylene), poly(4,4'-isopropylene diphenylene carbonate), poly(ethylene-vinyl esters), poly(ethylene-vinyl acetate), poly(vinyl chloride-diethyl fumarate), poly(esters of acrylic and methacrylic), partially hydrolyzed poly(vinyl acetate), poly(vinyl butyral), poly(amides), poly(vinyl carbonate), styrene-isoprene block copolymer, ethylene-propylene copolymer, ethylene propylene terpolymer, acrylonitrile-butadiene-styrene terpolymer, poly(olefins), poly(urethane) having a polyester or a polyether linkage, and the like. These polymers and their physical properties are known to the art and they can be synthesized according to the procedures disclosed in *Encyclopedia of Polymer Science and Technology,* Vol. 15, pages 508 to 530, 1971, published by Interscience Publishers, Inc., New York; *Polymers,* Vol. 17, 938 to 956, 1976; *Technical Bulletin,* SCR-159, 1965, Shell Corp., New York; and references cited therein.

The vaginal agent delivery diaphragm comprising the annular reservoir as provided herein can be manufactured from porous and microporous tubing made from thermoplastic polymers that can be melt extruded to form a tubing structure. In one process, a tube is produced from an extrudable thermoplastic polymeric composition, by extruding with a commercial extruder through a die, a thermoplastic polymer that includes a leachable additive of prepore forming size. Typical examples of leachable components are water soluble modified starches, and other water soluble polymers such as polyethylene oxides, polyvinyl alcohol, sodium alignate, gelatin, hydroxyethyl cellulose, urea, and the like. The tube after extrusion is subjected to a liquid which leaches the leachable additive resulting in a porous tube.

In another process a thermoplastic polymer and a leachable sintered powder are mixed and extruded through a die of known shape and dimensions. A representative sintered powder is prepared by blending for example, hydroxypropyl cellulose and polyethylene glycol, followed by sintering the blend in a high speed mixture at an elevated temperature. Next, a thermoplastic polymer and the powder are ground in a conventional grinder to a known sieve size. The blend is then extruded, and after extrusion the tube is subjected to intensive leaching or washing to produce a microporous structure in the tube wall. Another process for forming a porous tube comprises extruding in an extruder of a conventional type, and operated at a pressure needed for extrusion, a thermoplastic polymer and a blowing agent. Typical agents that create a foamed or a porous cellular structure include aryl-bis-sulfo-hydrazide, azodicarbonamide, azobisiso-butyronitrile, ammonium sesquicarbonate, and the like. The blowing agent releases gas and expands when the tube is exposed to a heat zone, which physical action and evolution of gas forms the porous structure. Procedures, equipment and materials suitable for manufacturing porous and microporous structures are known to the art in U.S. Pat. No. 3,223,761 issued to Raley; in U.S. Pat. No. 3,551,538 issued to Yamamoto et al; in U.S. Pat. No. 3,552,658 issued to Thomas; in U.S. Pat. No. 3,911,072 issued to Saito et al; and in U.S. Pat. No. 4,182,582 issued to Youval et al.

The microporous polymeric material can further be described as having pores that can be characterized as continuous pores interconnected through tortuous paths of regular and irregular shape. Generally, the final microporous materials can possess from 5 to 95% with a pore size which permits controlled release of the drug. Generally, a pore size of from 10 angstroms to 200 microns, or more, can be used for releasing the agent, with the micropores filling with a carrier through which the agent migrates to the exterior of the diaphragm. Materials useful for making microporous tubing includes the thermoplastic polymers described above and polymers such as polycarbonates, polyhexamethylene adipamide, polyolefins, polyalkylene sulfide, polyethers, polyesters, and like microporous homopolymers, copolymers and termpolymers.

The film of the vaginal diaphragm used to form the cup-shaped or dome-shaped member of the diaphragm as joined circumferentially to the annular reservoir, can in a preferred embodiment contain an active agent. The polymeric materials used for forming the film include those described above, and materials such as natural rubber, butyl rubber and the like. The active agent is incorporated in the polymeric material in a variety of manners, such as adding the active agent into the polymeric material during formation thereof, by immersing the film in a bath of saturated active agent solution that lets the film imbib the active agent, and the like.

Exemplary inner mass transfer conductors are carriers suitable for mixing with the active agent in the annular reservoir. These include liquid, semi-liquid carriers such as emulsions, gels, glycols, and the like. These carriers are permeable to the passage of agent, they are capable of containing dissolved and undissolved agent, and they are capable of forming a liquid carrier wall interface at the inner surface of the annular reservoir. Typical carriers include amember selected from the reservoir. Typical carriers include amember selected from the group consisting of mineral, animal, fruit, nut, plant, sylvan, inorganic and organic oils. The carrriers also include a member selected from the group consisting essentially of liquids, glycols, alkylene glycols, bisalkylene glycols, poly(alkylene glycols), poly(oxyalkylene)-poly(oxyalkylene) copolymer, aqueous gels, and the like. The carriers also include aqueous carriers include vegetable oil, marine oil, aqueous media such as water mixed with poly(alkylene glycols) including 400 to 6000, poly(propylene glycol) having a molecular weight of 500 to 2000, glycerol polysorbate 80, and the like. Examples of carriers are known to the art in *Pharmaceutical Sciences*, by Remington, 1970,published by Mack Publishing Company, Easton, PA.

The term active agent as used herein includes spermicides, germicides and virucides. The terms spermicide and spermicidal as used herein are intended to encompass agents that kill sperm, as well as those agents which immobilize or render sperm ineffective for their intended effect by their spermicide semen contact. In one embodiment the spermicides include anionic surface active spermicides, non-ionic surface active spermicides and cationic surface active spermicides, and mixtures thereof. Exemplary spermicides that can be released by the vaginal diaphragm are represented by the following: di-isobutylphenoxypolyethoxy ethanol, dodecaethylene glycol monolaurate p-methanylphenyl polyoxyethylene, methoxypolyoxyethylene glycol laurate, nonylphenoxy-polyethoxy ethanol, polyethylene glycol of monoisoctyl phenol ether, polyoxyethylenenonyl phenol, polyoxyethylene nonylphenol ether, aminopropanesulfonate, nonylphenol nonaethoxylate, tri-isopropyl-phenoxypolyethoxy ethanol, sodium lauryl sulfate, glyceryl monoricinolate, spermicidal mixtures such as methoxy-polyethylene glycol laurate and nonylphenoxypolyethoxyethanol, trioxymethylene and nonylphenoxy-polyoxyethylene ethanol, p-triisopropylphenoxypolyethoxyethanol and sodium lauryl sulfate, p-diisobutyl-phenoxypolyethoxyethanol and nonylphenoxypolyethoxyethanol, sodium sulfodioctyl succinate and triisopropylphenyloxypolyethoxyethanol, glyceryl monoricinoleate and triisopropylphenyloxypolyethoxyethanol, and the like. The amount of spermicide in the vaginal diaphragm can be up to 100%. The amount of spermicide in the diaphragm, when the spermicide is mixed with a mass transfer conductor, is about 0.5% to 80% by weight of the total ingredients in the vaginal diaphragm. The diaphragm, when in operation, releases a spermicidally effective amount of the spermicide over time, and more particularly from 50 microns to 500 milligrams per hour, or higher. The diaphragm releasing the spermicide can be positioned prior to intercourse in the vagina, and removed in a period of time after intercourse.

The term germicide includes the spermicides which are known for preventing sexually transmitted diseases as well as for their spermicidal activity, as reported in *Health*, page 19, December 1982; and in U.S. Pat. No. 4,309,997. The term germicide includes antibiotics such as gentamicin sulfate, penicillin, tetracycline hydrochloride and the like. The term viricide includes 2-deoxy-D-glucose, Acyclovir ® viricide, and the like. The term sexually transmissible disease includes the like. The term sexually transmissible disease includes *N. gonorrhea, Treponema pallidum, T. vaginalis, Candida albicans,* Herpes Simplex, and the like. The vaginal diaphragm delivers the minimum inhibitory concentration of active agent in vivo for preventing the transmittal of a veneral disease. The minimum inhibitory concentration is the therapeutically effective amount for the intended purpose.

The materials used for manufacturing the coupling member are generally physiologically inert materials. The coupling member can be made from the same material as the vaginal diaphragm, or the coupling member can be made from a different material than the materials used to make the vaginal diaphragm. The coupling member, when placed in a tubular wall forming the annular reservoir, has the same shape as the reservoir and it cooperates with the tube to form a single, annular reservoir. The coupling generally has a diameter measured across its cross-section equivalent to the inside diameter of the tubular member forming the reservoir. Typical materials for forming the coupling are those listed above. Also, the coupling can be made from a hydrophilic polymer, such as a sparingly to moderately cross-linked hydrogel that swells 5 to 20% when in place in the presence of a fluid carrier in the reservoir. Representative hydrophilic polymers include polyglycolmethacrylate, copolymeric diethylene glycolmethacrylate and methylmethacrylate, polyacrylonitrite, polymethacrylamide, polyhydroxylethylmethacrylate, and the like.

The coupling used for joining the two ends can be held in firm, fluid tight relation by solvent bonding, or by adhesive attachment. When a solvent is used, the surfaces of the coupling and the inside of the tube are moistened with an organic solvent that causes the surfaces to feel tacky, and when placed in contact the surfaces then bonds and adheres then into a fluid tight union. The ends of the member can be adhesively united to form a closed system by applying an adhesive substance to the surfaces that hold the ends together by surface attachment. For the above procedures, the solvent includes organic solvents such as methylene chloride, ethylene dichloride, trichlorobenzene, dioxan, isophorone, tetrahydrofuran, aromatic and chlorinated hydrocarbons, mixed solvents, such as 50/50 ethylene dichloride/diacetone alcohol; 40/60 alcohol/toluene; 30/70 alcohol/carbon tetrachloride, and the like. Suitable adhesives include natural adhesives and synthetic adhesives, such as animal, nitrocellulosic, polyamide, phenolic, amino, epoxy, isocyanate, acrylic, silicate, organic adhesives of polymers, and the like. The adhesives are known to the art in *The Encyclopedia of Chemistry*, 2nd Edition, edited by George L. Clark and Gressner G. Hawley, 1966, published by VanNostrand Reinhold Co., Cincinnati, Ohio; and the solvents are known in *Encyclopedia of Chemical Technology*, Kirk-Othmer, 2nd Edition, Vol. 16, 1969, published by Interscience, Publishers Inc., New York.

The following examples are merely illustrative of the present invention and they should not be considered as limiting the scope of the invention in any way, as these examples and equivalents thereof will become apparent to those versed in the art in the light of the present disclosure, the drawings and the accompanying claims.

EXAMPLE 1

An intravaginal diaphragm useful for the purposes of this invention is manufactured as follows: first, a premeasured section of styrene-butadiene block copolymer vaginally acceptable tubing is washed with water for 48 to 56 hours, and then dried in air at room temperature. Then, the tubing is cut into appropriate lengths and shaped like a ring, and molded into a torus at 165° C. Next, a solid polymeric plug made of the copolymer and having an outside diameter equivalent to the inside diameter of the tube is very lightly dampened with methylene chloride and inserted into the tube ends for joining the open tube at its two ends, thereby forming a closed annular reservoir.

Next, a film of the copolymer is preheated to a temperature below its melting point and placed on the annular reservoir preheated to a temperature below its melting point. To form the cup-shaped film of the diaphragm, the annular reservoir and the film are held in tight contact with each other causing the film to conform and send its cup-shape to the annular reservoir.

Next, a film of the copolymer is preheated to a temperature below its melting point and placed on the annular reservoir preheated to a temperature below its melting point. To form the cup-shaped film of the diaphragm, the annular reservoir and the film are held in tight contact with each other causing the film to conform and seal its cup-shape to the annular reservoir. The sealing or fusing of the film to the annular reservoir is instant on contact of the copolymeric members.

Next, the annular reservoir is filled with a germicide by injecting a germicide carrier formulation into the inner lumen through an inlet needle placed in the wall of the reservoir surrounding the lumen. The lumen is filled continuously until all the air in the lumen is displaced through a similar outlet needle placed in the wall of the reservoir. This procedure completely fills the annular reservoir. Finally, the needles are removed and the needle punctures closed with a few drops of methylene chloride. The germicide formulation comprises penicillin sodium and a sodium citrate, citric acid pharmaceutically acceptable liquid carrier.

EXAMPLE 2

The procedure of Example 1 is repeated with the coupling member inside the annular reservoir made of poly(vinylchloride) with a passage therethrough, or from cross-linked poly(glycolmethacrylate) with a passage therethrough. The couplings are positioned inside the tubular annular reservoir member and they extend from the ends of the annular reservoir a distance therein for imparting both structural support and continuity to the final manufactured closed annular reservoir. The cooperation of the coupling with the annular reservoir acts as a unit that provides a diaphragm suitable for intimate anatomical contact and for beneficial agent release in the vagina. The diaphragm is held in place by the resilient tension, that is, the spring tension of the annular rim, the vaginal muscle tone, and the pubic bone structure.

EXAMPLE 3

An annular reservoir is made by mixing 10 parts of polydimethylsiloxane base with 1 part of stannous octoate curing agent, deairating the mixture under vacuum, and then coating a mandrel with the mixture. The mixture is cured at 125° C. for 15 minutes to yield the elastomer. The cured polymer is stripped from the mandrel and a solid polymer silicone connector lightly coated with adhesive inserted into the elastomeric tube for joining its ends into a closed, annular reservoir.

Then, the annular reservoir is placed in a thermoforming female die and a dome-shaped sheet of polydimethylsiloxane overlayed on the annular reservoir. Next, a thermoforming convex male die is brought into contact with the female die in the form of a reciprocal cavity, and the two dies heated for permanently joining the film and the annular reservoir to yield a diaphragm. Then, the reservoir is filed by injection into the reservoir nonylphenoxypolyethoxy ethanol 30% by weight, in an aqueous carrier.

EXAMPLE 4

An annular reservoir comprising segmented copolymer of butylene terephthalate 33% and polytetramethylene ether terephthalate 67%, surrounding an internal lumen is made into a seamless endless reservoir by clamping the ends of an extruded tube to be joined in faced relation, bringing the ends together in the presence of radiant heat and maintaining the contacting ends together until they are fused into a unit reservoir. A film of segmented copolymer of butylene terephthalate 58% and polytetramethylene ether terephthalate is spread across the annular reservoir and thermally fused to the annular reservoir to yield the vaginal diaphragm. The annular reservoir is filled with a composition of nonylphenoxypolyethoxy ethanol in polyethylene glycol following the procedures described above.

EXAMPLE 5

The procedure of Example 4 is repeated with the annular reservoir and the cup-shaped film formed of a soft polyolefin thermoplastic polymer, the annular reservoir charged with nonylphenoxypolyethoxy ethanol and polyoxyethylenenoyl phenol ether in an aqueous carrier, the cup-shaped integral film coated with the spermicide composition, and the excess carrier removed from the film in vacuum. The vaginal diaphragm made according to the procedures is refillable or disposable.

EXAMPLE 6

The procedure of Example 5 is repeated with the annular reservoir and the dome-shaped film made of polyurethane, with the reservoir charged with nonoxynol 9 in polyethylene glycol 4000, and the dome-shaped film impregnated with nonoxynol 9 that is spontaneously activated in the vagina on contact with vaginal fluid. The diaphragm can also be made by vacuum forming by placing an annular reservoir in a female mold cavity that has a vacuum pump connected to the bottom of the mold, overlaying the mold with a dish shaped film, covering the circular reservoir with a heater, and then applying heat in order to draw the heated film into the mold. The film can be sprayed with the active agent to yield the vaginal diaphragm.

The vaginal diaphragm of the invention provides many advantages to the dispensing art. For example, the diaphragm can be made in many sizes for accommodating all users. The diaphragm can be made thin for containment in a purse package for ready availability. The diaphragm can be used without an applicator; the diaphragm is a self-contained spermicide dispenser; it is reusable or disposable, inexpensive, and is easy to manufacture. The vaginal diaphragm can be used for preventing conception in a female capable of conception, or as a method for producing a contraceptive, environment in a vagina of a woman desiring same. The method, in either case, comprises placing in the vagina a vaginal diaphragm that fits between the posterior aspect of the public bone, the posterior vaginal fornix and covers the cervix, with a diaphragm that comprises a wall that surrounds an internal lumen that contains an amount of a spermicide sufficient for producing a contraceptive effect over a long time, and has a film that extends across the area encompassed by the annular wall, and which diaphragm delivers the spermicide in a spermicidally effective amount to the vagina at a preprogrammed, continuous and controlled rate for producing the intended effect(s). The method further comprises (1) releasing a spermicide from the film concomitantly with release of spermicide from the annular lumen; and, (2) releasing the spermicide that acts in cooperation with the sperm impervious material properties of the diaphragm for producing the intended results. The vaginal diaphragm can be used also as a method for preventing venereal disease by delivering from the annular lumen, and from the film an effective amount of a vaginally acceptable venereal disease preventing agent for producing the intended effect.

In summary, the invention further provides a method for making a vaginal diaphragm by shaping a biocompatible tube to a shape and size adapted for placement in a vagina, by inserting into one end of the tube a coupling member, then forming a closed hollowed annular reservoir by inserting the remaining portion of the coupling into the other end of the tube, uniting a sheet of a thermoplastic, flexible elastomer having a perimeter greater than the perimeter of the annular reservoir to the annular reservoir, whereby a vaginal diaphragm is formed having a continuous integral reservoir with a flexible domed shaped diaphragm film, then admitting a beneficial agent into the reservoir and continuously filling the reservoir while letting air escape from the reservoir to provide the vaginal diaphragm.

It will be understood to those versed in the vaginal dispensing art, in the light of the present specification, drawing figures, and the accompanying claims, the invention makes available both a novel and useful vaginal diaphragm for delivering useful agents in the vagina. It will be further understood to those versed in the art that different embodiments of this invention can be made without departing from the spirit and the scope of the invention. Accordingly, it is to be understood the invention is not to be construed as limited, but embraces all equivalents inherent herein.

I claim:

1. A vaginal diaphragm adapted and sized for easy insertion and comfortable retention in a vagina, the vaginal diaphragm comprising: a tube member comprising a wall that surrounds an internal lumen, which tube member is united at its ends by an internal coupling member to define an annular internal reservoir, the wall of the tube member formed of a vaginally acceptable material that controls the rate of release of an active agent from the annular reservoir; a vaginally acceptable active agent formulation in the lumen; and, a dome-shaped film extended across the area encompassed by the annular reservoir, the film a flexible diaphragm secured to the annular reservoir and formed of a vaginally acceptable material.

2. The vaginal diaphragm adapted and sized for easy insertion and comfortable retention in the vagina according to claim 1, wherein the film has an area greater than the area within the annular reservoir.

3. The vaginal diaphragm adapted and sized for easy insertion and comfortable retention in the vagina according to claim 1, wherein the coupling member inserted into the annular reservoir comprises a solid polymer.

4. The vaginal diaphragm adapted and sized for easy insertion and comfortable retention in the vagina according to claim 1, wherein the coupling member has a passageway therethrough.

5. The vaginal diaphragm adapted and sized for easy insertion and comfortable retention in the vagina according to claim 1, wherein the film contains a vaginally acceptable active agent formulation.

6. The vaginal diaphragm adapted and sized for easy insertion and comfortable retention in the vagina according to claim 1, wherein the film is coated with a vaginally acceptable active agent formulation.

7. The vaginal diaphragm adapted and sized for easy insertion and comfortable retention in the vagina according to claim 1, wherein the film is impregnated with a vaginally acceptable active agent formulation.

8. The vaginal diaphragm adapted and sized for easy insertion and comfortable retention in the vagina according to claim 1, wherein the active agent comprising the vaginally acceptable active agent formulation is a spermicide.

9. The vaginal diaphragm adapted and sized for easy insertion and comfortable retention in the vagina according to claim 1, wherein the active agent comprising the vaginally acceptable active agent formulation is a germicide.

10. The vaginal diaphragm adapted and sized for easy insertion and comfortable retention in the vagina according to claim 1, wherein a tension member is present in the annular reservor.

11. The vaginal diaphragm adapted and sized for easy insertion and comfortable retention in the vagina according to claim 1, wherein the vaginal diaphragm is a disposable contraceptive.

12. The vaginal diaphragm adapted and sized for easy insertion and comfortable retention in the vagina according to claim 1, wherein the annular reservoir releases the active agent by diffusion.

13. The vaginal diaphragm adapted and sized for easy insertion and comfortable retention in the vagina according to claim 1, wherein the vaginally acceptable material forming the annular reservoir is a microporous material.

14. A vaginal diaphragm dimensioned and structured for easy insertion and comfortable retention in the vaginal cul-de-sac posterior and inferior to the cervix, the vaginal diaphragm comprising: an annular shaped tube formed of a chemically inert, thermoplastic polymer having a pair of ends seamlessly joined to form a closed, annular reservoir; a vaginally acceptable active agent formulation in the reservoir; and, a film covering the area embraced by the annular reservoir and secured to the annular reservoir, said film a flexible diaphragm adapted to cover the cervix when the vaginal diaphragm is positioned in the vagina.

15. The vaginal diaphragm dimensioned and structured for easy insertion and comfortable retention in a vagina according to claim 14, wherein a tension member is present in the annular reservoir.

16. The vaginal diaphragm dimensioned and structured for easy insertion and comfortable retention in a vagina according to claim 14 wherein the film contains a vaginally acceptable active agent formulation.

17. The vaginal diaphragm dimensioned and structured for easy insertion and comfortable retention in a vagina according to claim 14, wherein the film is coated with a vaginally acceptable active agent formulation.

18. The vaginal diaphragm dimensioned and structured for easy insertion and comfortable retention in a vagina according to claim 14, wherein the film is impregnated with a vaginally acceptable active agent formulation.

19. The vaginal diaphragm dimensioned and structured for easy insertion and comfortable retention in a vagina according to claim 14, wherein the active agent formulation in the reservoir comprises a spermicide.

20. The vaginal diaphragm dimensioned and structured for easy insertion and comfortable retention in a vagina according to claim 14, wherein the active agent formulation in the reservoir comprises a germicide.

21. The vaginal diaphragm dimensioned and structured for easy insertion and comfortable retention in a vagina according to claim 14, wherein the vaginal diaphragm is disposable.

22. The vaginal diaphragm dimensioned and structured for easy insertion and comfortable retention in a vagina according to claim 14, wherein the annular reservoir releases the active agent by diffusion.

23. The vaginal diaphragm dimensioned and structured for easy insertion and comfortable retention in a vagina according to claim 14, wherein the annular reservoir releases the active agent by a microporous process.

24. The vaginal diaphragm dimensioned and structured for easy insertion and comfortable retention in a vagina according to claim 14, wherein the film is impervious to sperm.

25. The vaginal diaphragm dimensioned and structured for easy insertion and comfortable retention in a vagina according to claim 1, wherein the film is impervious to sperm.

* * * * *